(12) United States Patent
Bagga et al.

(10) Patent No.: US 9,814,804 B2
(45) Date of Patent: *Nov. 14, 2017

(54) METHOD OF DOSE CONTROLLED APPLICATION OF BONE GRAFT MATERIALS BY WEIGHT

(71) Applicant: PROSIDYAN, INC., Warren, NJ (US)

(72) Inventors: Charanpreet S. Bagga, Basking Ridge, NJ (US); Hyun W. Bae, Los Angeles, CA (US)

(73) Assignee: PROSIDYAN, INC., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,558

(22) Filed: May 16, 2016

(65) Prior Publication Data

US 2016/0256609 A1 Sep. 8, 2016

Related U.S. Application Data

(63) Continuation of application No. 13/957,773, filed on Aug. 2, 2013, now Pat. No. 9,339,392.

(60) Provisional application No. 61/678,756, filed on Aug. 2, 2012.

(51) Int. Cl.

| | | |
|---|---|---|
| *A61F 2/28* | (2006.01) |
| *A61L 27/56* | (2006.01) |
| *A61F 2/46* | (2006.01) |
| *A61L 27/04* | (2006.01) |
| *A61L 27/12* | (2006.01) |
| *A61L 27/18* | (2006.01) |
| *A61F 2/30* | (2006.01) |

(52) U.S. Cl.
CPC .............. *A61L 27/56* (2013.01); *A61F 2/28* (2013.01); *A61F 2/4601* (2013.01); *A61L 27/047* (2013.01); *A61L 27/12* (2013.01); *A61L 27/18* (2013.01); *A61F 2/3094* (2013.01); *A61F 2002/2835* (2013.01); *A61F 2002/4663* (2013.01); *A61L 2430/02* (2013.01)

(58) Field of Classification Search
CPC ........ A61F 2/4601; A61F 2/28; A61F 2/3094; A61F 2/46

See application file for complete search history.

(56) References Cited

U.S. PATENT DOCUMENTS

| | | | |
|---|---|---|---|
| 5,716,413 A | 2/1998 | Walter | |
| 5,977,204 A | 11/1999 | Boyan | |
| 8,567,162 B2 | 10/2013 | Bagga et al. | |
| 9,339,392 B2 * | 5/2016 | Bagga | ................. A61F 2/4601 |
| 2001/0051833 A1 | 12/2001 | Walter | |
| 2008/0206186 A1 | 8/2008 | Butler | |
| 2009/0130174 A1 | 5/2009 | Guelcher | |
| 2010/0124583 A1 | 5/2010 | Medoff | |
| 2010/0137990 A1 | 6/2010 | Apatsidis | |
| 2011/0144763 A1 | 6/2011 | Bagga et al. | |
| 2011/0144764 A1 | 6/2011 | Bagga et al. | |
| 2011/0151027 A1 | 6/2011 | Clineff et al. | |
| 2012/0308825 A1 | 12/2012 | Ma et al. | |
| 2013/0338790 A1 | 12/2013 | Okimura | |
| 2014/0039640 A1 | 2/2014 | Bagga | |
| 2014/0294783 A1 | 10/2014 | Wen | |
| 2015/0273380 A1 | 10/2015 | Sakashita | |
| 2015/0342224 A1 | 12/2015 | Medoff | |

OTHER PUBLICATIONS

Woodruff et al., "Bone tissue engineering: from bench to bedside", Materials Today, 15(10), 2012, pp. 430-435.

* cited by examiner

*Primary Examiner* — Alvin Stewart
(74) *Attorney, Agent, or Firm* — MH2 Technology Law Group LLP

(57) ABSTRACT

Methods of providing dose controlled application of bone graft materials are disclosed. In particular, methods for determining a target quantity of bone graft material for clinical application in order to ensure maximum clinical results are provided. These methods comprise determining the target weight of the material to be applied.

25 Claims, No Drawings

METHOD OF DOSE CONTROLLED APPLICATION OF BONE GRAFT MATERIALS BY WEIGHT

CROSS-REFERENCE TO RELATED APPLICATIONS

This application is a continuation of U.S. application Ser. No. 13/957,773 filed Aug. 2, 2013, now U.S. Pat. No. 9,339,392, which application claims priority to U.S. Provisional No. 61/678,756, filed Aug. 2, 2012, and entitled "METHOD OF PROVIDING DOSE CONTROLLED APPLICATION OF BONE GRAFT MATERIAL," the contents of which are incorporated by reference in their entirety.

FIELD

The present disclosure relates generally to bone graft materials and methods of dose controlled application of such materials. More particularly, the present disclosure relates to methods for determining a target quantity of bone graft material for clinical application in order to ensure maximum clinical results.

BACKGROUND

The role of bone graft materials in clinical applications to aid the healing of bone has been well documented over the years. Most bone graft materials that are currently available, however, have failed to deliver the anticipated results necessary to make these materials a routine therapeutic application in reconstructive surgery. Improved bone graft materials for forming bone tissue implants that can produce reliable and consistent results are therefore still needed and desired.

In recent years intensive studies have been made on bone graft materials in the hopes of identifying the key features necessary to produce an ideal bone graft scaffold, as well as to proffer a theory of the mechanism of action that results in successful bone tissue growth. At least one recent study has suggested that a successful bone tissue scaffold should consider the physicochemical properties, morphology and degradation kinetics of the bone being treated. ("Bone tissue engineering: from bench to bedside", Woodruff et al., Materials Today, 15(10): 430-435 (2012)). According to the study, porosity is necessary to allow vascularization, and the desired scaffold should have a porous interconnected pore network with surface properties that are optimized for cell attachment, migration, proliferation and differentiation. At the same time, the scaffold should be biocompatible and allow flow transport of nutrients and metabolic waste. Just as important is the scaffold's ability to provide a controllable rate of biodegradation to compliment cell and/or tissue growth and maturation. Finally, the ability to model and/or customize the external size and shape of the scaffold is to allow a customized fit for the individual patient is of equal importance.

Woodruff, et. al. also suggested that the rate of degradation of the scaffold must be compatible with the rate of bone tissue formation, remodeling and maturation. Recent studies have demonstrated that initial bone tissue ingrowth does not equate to tissue maturation and remodeling. Accord to the study, most of the currently available bone graft materials are formulated to degrade as soon as new tissue emerges, and at a faster rate than the new bone tissue is able to mature, resulting in less than desirable clinical outcomes.

Other researchers have emphasized different aspects as the core features of an ideal bone graft material. For example, many believe that the material's ability to provide adequate structural support or mechanical integrity for new cellular activity is the main factor to achieving clinical success, while others emphasize the role of porosity as the key feature. The roles of porosity, pore size and pore size distribution in promoting revascularization, healing, and remodeling of bone have long been recognized as important contributing factors for successful bone grafting implants. Many studies have suggested an ideal range of porosities and pore size distributions for achieving bone graft success. However, as clinical results have shown, a biocompatible bone graft having the correct structure and mechanical integrity for new bone growth or having the requisite porosities and pore distributions alone does not guarantee a good clinical outcome. What is clear from this collective body of research is that the ideal bone graft implant should possess a combination of structural and functional features that act in synergy to allow the bone graft implant to support the biological activity and an effective mechanism of action as time progresses.

Currently available bone graft materials fall short of meeting these requirements. That is, many bone graft materials tend to suffer from one or more of the problems previously mentioned, while others may have different, negatively associated complications or shortcomings. One example of such a graft material is autograft material. Autograft materials have acceptable physical and biological properties and exhibit the appropriate mechanical structure and integrity for bone growth. However, the use of autogenous bone requires the patient to undergo multiple or extended surgeries, consequently increasing the time the patient is under anesthesia, and leading to considerable pain, increased risk of infection and other complications, and morbidity at the donor site.

When it comes to synthetic bone graft substitutes, the most rapidly expanding category consists of products based on calcium sulfate, hydroxyapatite and tricalcium phosphate. Whether in the form of injectable cements, blocks or morsels, these materials have a proven track record of being effective, safe bone graft substitutes for selected clinical applications. Recently, new materials such as bioactive glass ("BAG") materials have become an increasingly viable alternative or supplement to natural bone-derived graft materials. In comparison to autograft materials, these new synthetic materials have the advantage of avoiding painful and inherently risky harvesting procedures on patients. Also, the use of these synthetic, non-bone derived materials can reduce the risk of disease transmission. Like autograft and allograft materials, these new artificial materials can serve as osteoconductive scaffolds that promote bone regrowth. Preferably, the graft material is resorbable and is eventually replaced with new bone tissue.

Many artificial bone grafts available today comprise materials that have properties similar to natural bone, such as implants containing calcium phosphates. Exemplary calcium phosphate implants contain type-B carbonated hydroxyapatite whose implant in general may be described as $(Ca_5(PO_4)_{3x}(CO_3)_x(OH))$. Calcium phosphate ceramics have been fabricated and implanted in mammals in various forms including, but not limited to, shaped bodies and cements. Different stoichiometric implants, such as hydroxyapatite (HA), tricalcium phosphate (TCP), tetracalcium phosphate (TTCP), and other calcium phosphate (CaP) salts and minerals have all been employed in attempts to match the adaptability, biocompatibility, structure, and strength of natural bone. Although calcium phosphate based materials are widely accepted, they lack the ease of handling, flexibility and capacity to serve as a liquid carrier/storage media necessary to be used in a wide array of clinical applications. Calcium phosphate materials are inherently rigid, and to facilitate handling are generally provided as part of an admixture with a carrier material; such admixtures typically have an active calcium phosphate ingredient to carrier volume ratio of about 50:50, and may have a ratio as low as 10:90.

As previously mentioned, the roles of porosity, pore size and pore size distribution in promoting revascularization, healing, and remodeling of bone have been recognized as important contributing factors for successful bone grafting materials. Yet currently available bone graft materials still lack the requisite chemical and physical properties necessary for an ideal graft material. For instance, currently available graft implants tend to resorb too quickly (e.g., within a few weeks), while some take too long (e.g., over years) to resorb due to the implant's chemical composition and structure. For example, certain implants made from hydroxyapatite tend to take too long to resorb, while implants made from calcium sulfate or β-TCP tend to resorb too quickly. Further, if the porosity of the implant is too high (e.g., around 90%), there may not be enough base material available. Conversely, if the porosity of the material is too low (e.g., 10%) then too much material must be resorbed, leading to longer resorption rates. In addition, the excess material means there may not be enough room left in the residual graft implant for cell infiltration. Other times, the graft implants may be too soft, such that any kind of physical pressure exerted on them during clinical usage causes them to lose the fluids retained by them.

Improved bone graft materials that provide the necessary biomaterial, structure and clinical handling necessary for optimal bone grafting have previously been disclosed by applicants in U.S. Patent Application Publication No. 2011/0144764 entitled "BONE GRAFT MATERIAL", U.S. Patent Application Publication No. 2011/0144763 entitled "DYNAMIC BIOACTIVE BONE GRAFT MATERIAL HAVING AN ENGINEERED POROSITY", U.S. Patent Application Publication No. 2011/0140316 entitled "DYNAMIC BIOACTIVE BONE GRAFT MATERIAL AND METHODS FOR HANDLING", U.S. patent application Ser. No. 13/830,629 entitled "BIOACTIVE POROUS BONE GRAFT IMPLANTS", U.S. patent application Ser. No. 13/830,763 entitled "BIOACTIVE POROUS BONE GRAFT COMPOSITIONS IN SYNTHETIC CONTAINMENT", and U.S. patent application Ser. No. 13/830,851 entitled "BONE GRAFT IMPLANTS CONTAINING ALLOGRAFT."

These bone graft materials provide an improved mechanism of action for bone grafting by allowing the new tissue formation to be achieved through a physiologic process rather than merely from templating. These bone graft materials and resultant implants formed from these materials are engineered with a combination of structural and functional features that act in synergy to allow the bone graft implant to support cell proliferation and new tissue growth over time. The bone graft implants serve as cellular scaffolds to provide the necessary porosity and pore size distribution to allow proper vascularization, optimized cell attachment, migration, proliferation, and differentiation. The bone graft implants are formed of synthetic materials that are biocompatible and offer the requisite mechanical integrity to support continued cell proliferation throughout the healing process. In addition, the bone graft materials are formulated for improved clinical handling and allow easy modeling and/or customization of the external size and shape to produce a customized implant for the anatomic site.

While these improved graft materials are ideal for providing the many beneficial advantages currently lacking in available graft materials, yet without the negative complications associated with other graft materials, they nevertheless pose a different, more unique challenge for the user. Similar to many other compressible and/or expandable or pliable graft materials, including fiber-based bone graft materials, due to their tremendous pliability and flexibility, the manner of handling these materials becomes as important as the composition of the materials themselves. More specifically, due to the pliable nature of certain compressible and/or expandable or pliable graft materials, which may be easily compressible and expandable, it is desirable to provide a manner of consistently delivering a known quantity of fibrous material thereby providing a final implantable device possessing the desired target porosity. Thus, the ability to control the ultimate or final porosity of the fibrous materials becomes paramount. Inconsistent application of the fibrous material, which affects the ultimate porosity of the implant, may result in unpredictable and less desirable clinical outcomes. Accordingly, there exists a need for dosage control of these bone graft materials. Embodiments of the present disclosure address these and other needs.

SUMMARY

The natural process of tissue or wound healing is a dynamic, multi-dimensional cascade of bioactive events, with each successive event being dictated by the current physical environment (which is constantly changing over time as healing progresses) as well as the cascade's previous events. Therefore, ideal bone graft materials and implants formed from these materials need to be engineered with a combination of structural and functional features that act in synergy to allow the bone graft implant to support cell proliferation and new tissue growth over time. The implants need to provide the necessary porosity and pore size distribution to allow proper vascularization, optimized cell attachment, migration, proliferation, and differentiation. Not only do these implants need to be biocompatible, but also offer the requisite mechanical integrity to support continued cell proliferation throughout the healing process.

In order to meet the demands of this complex process, many bone graft materials are formulated to be moldable, or compressible and/or expandable. These materials may exist in a pliable state, such as in an expandable and/or compressible fibrous or granular network, foam, or otherwise. The ability to compress or expand the bone graft material improves clinical handling and allows easy modeling and/or customization of the external size and shape of the implants to produce a customized implant for the anatomic site. However, the compressible and/or expandable nature of the material also presents a unique challenge to the user or clinician. Exactly how much material should be used to produce the ultimate graft implant is determined by a number of factors, including the anatomical site to be treated, the size of the site, the shape of the site, in addition to the physicochemical properties of the graft material such as its porosity and pore size distribution. Without specific parameters guiding usage of the materials, the amount of actual graft material comprising these implants could vary widely from user to user, and from one day to another. For instance, the same clinician could create a more dense fibrous implant for one patient one day, a less dense fibrous implant for another patient another day, simply by making a best-guess as to how much material to use, or by using the physical constraints of the site to determine how much material will be needed, depending on the user's preferences for packing the material, without taking heed to the actual physicochemical requirements of the implant based on the actual site to be treated.

Accordingly, the present disclosure provides several embodiments of methods for ensuring that the correct quantity of bone graft material is used to produce the graft implant that is to be clinically applied. Methods of providing consistent, dose controlled application of compressible and/or expandable, pliable bone graft materials are disclosed. In particular, methods for determining a target quantity of bone graft material for clinical application of the material in order to ensure maximum clinical results are disclosed. These methods comprise determining the target weight of the material to be applied.

The roles of porosity, pore size and pore size distribution in promoting revascularization, healing, and remodeling of bone have long been recognized as important contributing factors for successful bone grafting implants. Many studies have suggested an ideal range of porosities and pore size distributions for achieving bone graft success. Several embodiments are disclosed for controlling the dosage or porosity of the bone graft material to achieve a desired dosage or porosity suitable for a particular defect.

In one embodiment, a method of treating a defect is provided. The method comprises providing a compressible and/or expandable, porous graft material. In one example, the graft material may comprise fibers or a fibrous network capable of compression and/or expansion (i.e., movement relative to one another). In another example, the graft material may be a combination of fibers and particulate or granules. In still another example, the bone graft material may comprise compressible and/or expandable particulate or granules. Next, the target porosity value of the material is calculated. The target porosity value should be determined based on the bone defect. The total weight of the material can be calculated, and finally a quantity representing the determined target weight of the graft material may be provided for implantation. The defect may be a bone defect, and the graft material may be bone graft material.

In another embodiment, a method of preparing a graft implant for implantation into a defect is provided. The method comprises providing a compressible and/or expandable, porous, graft material. Next, the target porosity value of the material is calculated. The target porosity value should be determined based on the defect. The total weight of the material can be calculated, and finally a quantity representing the determined target weight of the graft material may be used to form the implant. The defect may be a bone defect, and the graft material may be bone graft material.

In still another embodiment, a method of providing a graft material by weight is provided. The method comprises: determining a target porosity value for a graft implant for treating a defect; calculating a target weight for the amount of graft material to be used for the defect; and providing an amount of graft material representing the target weight in a sterile container. The graft material may be a bone graft material for use in treating bone defects.

It is to be understood that both the foregoing general description and the following detailed description are exemplary and explanatory only and are not restrictive of the disclosure. Additional features of the disclosure will be set forth in part in the description which follows or may be learned by practice of the disclosure.

DETAILED DESCRIPTION OF THE EMBODIMENTS

The standard method for healing natural tissue with synthetic materials has been to provide a device having the microstructure and macrostructure of the desired end product. Where the desired end product is cancellous bone, traditional bone grafts have been engineered to mimic the architecture of cancellous bone. Although this has been the current standard for bone grafts, it does not take into account the fact that bone is a living tissue. Each bony trabeculae is constantly undergoing active biologic remodeling in response to load, stress and/or damage. In addition, cancellous and cortical bone can support a vast network of vasculature. This network not only delivers nutrients to sustain the living environment surrounding bone, but also supports red blood cells and marrow required for basic biologic function. Therefore, merely providing a synthetic material with the same architecture that is non-biologic is insufficient for optimal bone healing and bone health. Instead, what is required is a mechanism that can recreate the living structure of bone.

Traditional synthetics act as a cast, or template, for normal bone tissue to organize and form. Since these synthetics are not naturally occurring, eventually the casts or templates have to be resorbed to allow for normal bone to be developed. If these architectured synthetics do not resorb and do not allow proper bone healing, they simply become foreign bodies that are not only obstacles, but potentially detrimental, to bone healing. This phenomenon has been observed in many studies with slow resorbing or non-resorbing synthetics. Since these synthetics are just chemically inert, non-biologic structures that only resemble bone, they behave as a mechanical block to normal bone healing and development.

With the understanding that bone is a living biologic tissue and that inert structures will only impede bone healing, a different physiologic approach is presented with the present invention. Healing is a phasic process starting with some initial reaction. Each phase builds on the reaction that occurred in the prior phase. Only after a cascade of phases does the final development of the end product occur—new bone tissue. The traditional method has been to replace or somehow stimulate healing by placing an inert final product as a catalyst to the healing process. This premature act certainly does not account for the physiologic process of bone development and healing.

The physiologic process of bone healing can be broken down to three phases: (a) inflammation; (b) osteogenesis; and (c) remodeling. Inflammation is the first reaction to injury and a natural catalyst by providing the chemotactic factors that will initiate the healing process. Osteogenesis is the next phase where osteoblasts respond and start creating osteoid, the basic material of bone. Remodeling is the final phase in which osteoclasts and osteocytes then recreate the three-dimensional architecture of bone.

In a normal tissue repair process, at the initial phase a fibrin clot is made that provides a fibrous architecture for cells to adhere. This is the cornerstone of all connective tissue healing. It is this fibrous architecture that allows for direct cell attachment and connectivity between cells. Ultimately, the goal is to stimulate cell proliferation and osteogenesis in the early healing phase and then allow for physiologic remodeling to take place. Since the desired end product is living tissue, the primary objective is to stimulate as much living bone as possible by enhancing the natural fiber network involved in initiation and osteogenesis as well as angiogenesis. With the understanding that bone is a living biologic tissue and that inert structures will only impede bone healing, a different physiologic approach is presented with the present invention. Healing is a phasic process starting with some initial reaction. Each phase builds on the reaction that occurred in the prior phase. Only after a cascade of phases does the final development of the end product occur—bone. The traditional method has been to replace or somehow stimulate healing by placing an inert final product as a catalyst to the healing process. This premature act certainly does not account for the physiologic process of bone development and healing.

The physiologic process of bone healing can be broken down to three phases: (a) inflammation; (b) osteogenesis; and (c) remodeling. Inflammation is the first reaction to injury and a natural catalyst by providing the chemotactic factors that will initiate the healing process. Osteogenesis is the next phase where osteoblasts respond and start creating osteoid, the basic material of bone. Remodeling is the final phase in which osteoclasts and osteocytes then recreate the three-dimensional architecture of bone.

In a normal tissue repair process, at the initial phase a fibrin clot is made that provides a fibrous architecture for cells to adhere. This is the cornerstone of all connective tissue healing. It is this fibrous architecture that allows for direct cell attachment and connectivity between cells. Ultimately, the goal is to stimulate cell proliferation and osteogenesis in the early healing phase and then allow for physiologic remodeling to take place. Since the desired end product is a living tissue and not an inert scaffold, the primary objective is to stimulate as much living bone as possible by enhancing the natural fiber network involved in initiation and osteogenesis.

The natural process of tissue or wound healing is a dynamic, multi-dimensional cascade of bioactive events, with each successive event being dictated by the current physical environment (which is constantly changing over time as healing progresses) as well as the cascade's previous events. Therefore, ideal bone graft materials and implants formed from these materials need to be engineered with a combination of structural and functional features that act in synergy to allow the bone graft implant to support cell proliferation and new tissue growth over time. The implants need to provide the necessary porosity and pore size distribution to allow proper vascularization, optimized cell attachment, migration, proliferation, and differentiation. Not only do these implants need to be biocompatible, but also offer the requisite mechanical integrity to support continued cell proliferation throughout the healing process.

In order to meet the demands of this complex process, many bone graft materials are formulated to be moldable, or compressible and/or expandable. These materials may exist in a pliable state, such as in an expandable and/or compressible fibrous or granular network, foam, or otherwise. The ability to compress or expand the bone graft material improves clinical handling and allows easy modeling and/or customization of the external size and shape of the implants to produce a customized implant for the anatomic site.

As mentioned, improved bone graft materials and bone graft implants formed from these materials have previously been disclosed in U.S. Patent Application Publication No. 2011/0144764 entitled "BONE GRAFT MATERIAL", U.S. Patent Application Publication No. 2011/0144763 entitled "DYNAMIC BIOACTIVE BONE GRAFT MATERIAL HAVING AN ENGINEERED POROSITY", U.S. Patent Application Publication No. 2011/0140316 entitled "DYNAMIC BIOACTIVE BONE GRAFT MATERIAL AND METHODS FOR HANDLING", U.S. patent application Ser. No. 13/830,629 entitled "BIOACTIVE POROUS BONE GRAFT IMPLANTS", U.S. patent application Ser. No. 13/830,763 entitled "BIOACTIVE POROUS BONE GRAFT COMPOSITIONS IN SYNTHETIC CONTAINMENT", and U.S. patent application Ser. No. 13/830,851 entitled "BONE GRAFT IMPLANTS CONTAINING ALLOGRAFT", all of which are co-pending and co-owned by applicants, the contents of which are incorporated herein by reference.

In some embodiments, these bone graft implants attempt to recapitulate the normal physiologic healing process by presenting the fibrous structure of the fibrin clot. Since these bioactive implants are both osteoconductive as well as osteostimulative, the fibrous network will further enhance and accelerate bone induction. Further, the free-flowing nature of the bioactive fibrous matrix or scaffold allows for natural initiation and/or stimulation of bone formation rather than placing a rigid template that may impede final formation as with current graft materials. The material can also be engineered to provide a chemical reaction known to selectively stimulate osteoblast proliferation or other cellular phenotypes.

In addition, some of these bone graft materials are formulated to be moldable, or compressible and/or expandable. The materials may exist in a pliable state, such as in an expandable and/or compressible fibrous or granular network, foam, or otherwise. The ability to compress or expand the bone graft material improves clinical handling and allows easy modeling and/or customization of the external size and shape of the implants to produce a customized implant for the anatomic site.

While these improved graft materials are ideal for providing the many beneficial advantages currently lacking in available graft materials (without the negative complications associated with other graft materials), they nevertheless pose a different, more unique challenge for the user. Like with many other pliable or moldable bone graft materials, due to the tremendous pliability and flexibility of these materials, what has become evident is that the manner of handling fiber-based materials becomes as important as the composition of the materials themselves. More specifically, due to the pliable nature of these graft materials, which may be easily compressible and/or expandable, it is desirable to provide a manner of consistently delivering a known quantity of fibrous material having a known porosity gradient as a final implant product. Thus, the ability to control the ultimate or final porosity of the fibrous materials becomes paramount. Inconsistent application of the fibrous material, which affects the ultimate porosity of the material, may result in unpredictable clinical outcomes.

For example, by way of background, freshly manufactured bioactive glass fibers of the kind previously disclosed by applicants are loosely packed and are approximately 95 to 97% porous, making the material air-like in consistency, similar to cotton candy. These fibers can be easily compressed and molded to various levels of porosity. The fibers may also settle over time and lose porosity due to gravitational forces compressing the fibers together (i.e., deflation). Accordingly, for any given medical or clinical procedure, it is recommended that a specific fiber density range be established. Without a specific fiber density range, variability will exist in the amount of fibers used from one defect site to another, and from one application to a different application. Such variability could leave to unpredictable, and more importantly, undesirable clinical outcomes. For instance, under dosage can lead to incomplete healing, while over dosage (i.e., overpacking the material into the defect site, for example) could impede the healing process. In an application where there is over dosage, the fibrous graft material itself may actually stand in the way of the healing, potentially delaying or even compromising the healing process.

Accordingly, the present disclosure provides several embodiments of methods for ensuring that the correct quantity of bone graft material is used to produce the graft implant that is to be clinically applied. Methods of providing consistent, dose controlled application of compressible and/or expandable, pliable bone graft materials are disclosed. In particular, methods for determining a target quantity of bone graft material for clinical application in order to ensure maximum clinical results are disclosed. These methods comprise determining the target weight of the material to be applied.

In one embodiment, a method of treating a bone defect is provided. The method comprises providing a compressible and/or expandable bone graft material. In one example, the bone graft material may comprise fibers capable of movement relative to one another. In another example, the bone graft material may be a combination of fibers and particulate or granules. In still another embodiment, the bone graft material may comprise particulate or granules.

Next, the target porosity value of the implant is calculated. The target porosity value should be determined based on the bone defect. The total weight of the material can be calculated, and finally a quantity representing the determined target weight of the bone graft material may be provided for implantation.

In one application, the bone graft material may be packaged by weight instead of volume. It is contemplated that surgical techniques would need to specify the preferred weight of the graft material to be used. Such weight could be determined based on any number of factors, including the defect size and location. For example, a chart listing the defect size for a specific location with corresponding recommended fiber dosage (by weight) may be provided for convenient reference. One exemplary dosage reference chart is provided below:

| Defect Diameter | Weight of material (grams/cm length of defect) |
|---|---|
| 1 cm | 0.5 to 1.0 |
| 2 cm | 2.0 to 4.0 |
| 3 cm | 4.5 to 9.0 |

Based on the diameter of the defect to be treated, the weight of the fibrous graft material may be determined. During the procedure, the appropriately packaged weight of material would be applied to the defect as a manner of controlling the dosage or density of the material. The values in the chart represent the fact that the relationship of fiber dosage to defect size may not always be a 1:1 ratio; accordingly, it is important to be able to provide the appropriate fiber density to allow for enhanced bone healing.

In other embodiments, the weight of the fibrous graft material can be determined on any number of physical parameters of the bone defect, such as dimension, size, geometry, volume, surface area, anatomic location, or extent of damage. The target weight of the material to be implanted may be calculated using a mathematical algorithm that takes into account the physical parameter of the bone defect. Or, as previously mentioned, the target weight may be determined by referring to a chart whereby predetermined weight ranges based on the physical parameter of the bone defect have already been established.

In another embodiment, the fibrous bone graft material can be packaged by weight, with a prescribed use per unit volume of the defect. In this example, the volume of the defect may be considered the physical parameter. For instance, a prescribed use of 0.5 to 1.0 grams of fibrous material per cc of defect can be provided.

In still another embodiment, the fibrous bone graft material can be provided in a pre-compressed state. In this pre-compressed state, the density may be such that the fibers are already settled, not in a state of settling. For example, the fibrous graft material may be pre-compressed from 97% porosity to about 90% porosity so that the materials may be able to hold their shape and will not deform further unless additional pressure is applied. The shape stable density may depend at least in part upon the diameter of the fibers. The smaller the diameter of the fibers, the larger the shape stable density would need to be, as smaller fibers will tend to have lower mechanical strength and can buckle under their own weight.

In yet another embodiment, the fibrous bone graft material may be provided in packaging containers of known volume. The containers would be filled with a known weight of the fibers so that a known density of the material is packaged for use.

In even still another embodiment, the fibrous bone graft material can be pre-compressed to a desired density and rolled into a sheet for packaging and use.

It is understood that different challenges of healing exist for different types of defects. These different challenges dictate the rate of absorption required of the graft material as well as the target porosity. Take, for example, the different requirements for a spinal interbody fusion, compared to a metaphyseal bone void fill, and compared to a posterolateral fusion, using the same graft material. Each of these bone healings takes place in a different anatomical region of the body, and therefore has different environmental constraints. One region could have a better connecting source of nutrients, while another region may have less access to nutrients. Accordingly, each location would require different characteristics of the same graft material to produce an ideal clinical outcome. In other words, a one-size-fits-all scenario does not result in the best chances of healing in these different bone healing examples.

Starting with the same underlying graft material, in the case of the spinal interbody fusion, the natural environment surrounding this kind of defect (vertebral endplates) provides a good source of cells and nutrients for healing, thus relatively greater porosity is desired and consequently less of the graft material (i.e., less density of material) needs to be used compared to a posterolateral fusion. In the case of the posterolateral fusion, relatively more material needs to be used because you want a denser implant that is slower to resorb, hence less porosity is required with this type of fusion. A metaphyseal defect would require the least amount of material (i.e., least dense implant of all three graft implants), since this is the least challenging of the three bone graft applications discussed.

The embodiments of the present disclosure recognize that several factors go into the determination of the target porosity value. For example, the target porosity value may be determined according to a physical parameter of the bone defect, such as dimension, size, geometry, volume, total surface area, anatomic location, or extent of damage. Based on these factors, certain predetermined target values may be accorded to the bone graft material for specific clinical usage. For example, taking the above example of the three kinds of bone healing, it is possible provide a scale or reference chart with recommended dosages for a particular bone graft material for a particular size defect and type of fusion.

As shown below, an exemplary guide may be provided, such as for example, for a spinal interbody fusion using a 45S5 material, a type of bioactive glass described in the applications cited above as well as in other literature. Taking into account the specific type of healing desired, the physical parameters of the defect, and the candidate material, it may be possible to provide the clinician with a recommended guidance or dosage chart to ascertain the appropriate target porosity value for the fusion. One exemplary dosage reference chart is provided below:

| Spinal Interbody Fusion using 45S5 Material | |
| --- | --- |
| Defect Volume | Target Porosity Value (+/−2.5%) |
| 5 cc or less | 80% |
| 5-10 cc | 75% |
| 10 cc or more | 70% |

This chart reflects the fact that, the smaller the defect size, the easier or faster the healing process. Therefore porosity can be higher with a smaller defect, as less material needs to be present to sustain the physical infrastructure necessary to complete the healing process. It is contemplated that such a chart could be provided for a particular defect of a specific anatomical region or location.

Once the target porosity value is established, the weight of the graft material can be calculated using the material's density value. By providing a method of controlling dose application that is dependent upon the weight of the material, the present embodiments provide a very simple, repeatable and reliable manner of calculating the amount of graft material needed for any particular defect. The following examples serve to explain the rationale for the weight-based theory of application of porous bone graft material of the present disclosure:

Example 1

A bone defect has a volume of 10 cc. The clinician has identified a particular bone graft material, such as for example 45S5 bone graft material (comprising bioactive glass fibers only) of the type previously disclosed by applicants, as having the appropriate physiochemical properties and structural integrity to heal this defect. The target porosity can be determined, such as by referencing a dosage chart similar to the one above. The clinician then makes a calculation to determine the weight of material to apply, as follows:

45S5 material density=2.7 grams/cc
Volume of defect=10 cc
Target porosity=70%

| Volume occupied by material = 30% or 3 cc |
| --- |
| Weight of material to be implanted = 3 × 2.7 g/cc = 8.1 grams |

In the previous example, the material comprised just fibers. However, the same principles and steps would apply equally if the material comprised a composite having some compressible and/or expandable components and some non-compressible and/or non-expandable components. In other words, even if the material comprised fibers and particulates or granules, the same weight would be needed for this material as would be needed for a fiber-only material, assuming these two materials had the same density value of 2.7 grams/cc of volume of defect, and the defects were the same. These examples show how the clinician can use a simple factor such as weight to determine the amount of material, or dosage of material, to be implanted into any particular defect. Thus, the methods disclosed are independent of the actual graft material, and can be utilized so long as the density of the material is known.

In some cases, the graft material can be shipped and/or sold, or otherwise provided in an already pre-weighed form in accordance with the recommended dosage chart or guide. For example, using the example above, 8.1 grams of 45S5 material can be packaged in a sterile 10 cc container or vial. Thus, the material can be packaged and shipped in a pre-weighed form that is ready for use, such as for example, to fill a bone void, where the defect volume is 10 cc. A series of pre-weighed containers or vials corresponding to the recommended dosage chart above could be provided to a clinician, so that the clinician could readily use a pre-weighed 5 cc vial of material for a 5 cc or less volume defect, for instance.

It is, of course, contemplated that the clinician could follow the recommended dosage of graft material as provided in the charts or reference guides discussed above, but is not restricted by these recommendations. Depending on the patient's particular needs, the clinician could elect a more aggressive approach, or conversely a more conservative approach. In some situations, the clinician may elect to modify the treatment by using a biological agent in conjunction with the graft material, for example. The biological agent may be one that accelerates healing, such as for example, bone morphogenic protein, growth factors, stem cells, etc. In this aggressive approach, the clinician may therefore desire increased porosity in the graft, and make the selection of dosage (i.e., amount of material by weight) based on this desire for more porosity. Alternatively, should the clinician elect a more conservative approach, he or she may desire a graft with a lower porosity, or higher density, with a relatively slower healing rate. This kind of conservative treatment may be suitable for older patients, or for smokers, for example, where the clinician does not want the graft to resorb too quickly. In these scenarios, the clinician could move up or down one or more levels on the recommended dosage chart to determine the correct weight of the desired graft to be used.

The methods contemplated address the unmet need for a manner of controlling dosage of fibrous, pliable and deformable bone graft materials irrespective of the composition of the materials. Although the present methods are described for use with applicants' previously disclosed fibrous bone graft materials, it is understood that the methods of the present invention are equally applicable to any graft material that is compressible and/or expandable, or moldable. Further, the methods are not limited to bone graft materials for bone defects, and can be practiced with all types of graft materials that are expandable or compressible, and for other defects, without limitation.

Other embodiments of the disclosure will be apparent to those skilled in the art from consideration of the specification and practice of the disclosure provided herein. It is intended that the specification and examples be considered as exemplary only.

What is claimed is:

1. A method of providing consistent, dose controlled application of a graft material to a defect, comprising:
providing a compressible or expandable, porous graft material;
determining a density value of the graft material;
calculating a target weight of a quantity of the graft material to be applied based on the determined density value; and
applying the quantity of graft material representing the target weight calculated to the defect.

2. The method of claim 1, further comprising the step of forming a graft implant from the quantity of graft material representing the target weight calculated prior to the applying step.

3. The method of claim 1, wherein the step of calculating a target weight comprises determining the porosity of the graft material.

4. The method of claim 3, wherein the step of calculating a target weight comprises determining a percentage value of volume occupied by the graft material.

5. The method of claim 4, further including the step of molding the graft material into a shape corresponding to the determined percentage value of volume.

6. The method of claim 1, wherein the graft material is in the form of fibers, particles, granules, clusters, or combinations thereof.

7. The method of claim 1, wherein the graft material comprises silicone, calcium, sodium, or phosphate.

8. The method of claim 1, wherein the defect is a bone defect, and the graft material comprises bone graft material.

9. A method of providing consistent, dose controlled application of a compressible or expandable, porous graft material to a defect, comprising:
providing a dosage reference chart comprising:
a physical parameter of the defect; and
a corresponding recommended attribute of the graft material, the attribute being either of a recommended dosage by weight or a target porosity value;
performing a clinical evaluation to determine the physical parameter of the defect;
referencing the chart to determine the required attribute of the graft material for the determined physical parameter of the defect; and
applying a quantity of graft material having the required attribute to the defect.

10. The method of claim 9, wherein the physical parameter comprises a dimension, size, geometry, volume, surface area, anatomic location, or extent of damage.

11. The method of claim 9, wherein the dosage chart is for a defect in a specific anatomical location.

12. The method of claim 9, further comprising the step of forming a graft implant from the quantity of graft material having the required attribute prior to the applying step.

13. The method of claim 9, wherein the graft material is in the form of fibers, particles, granules, clusters, or combinations thereof.

14. The method of claim 9, wherein the graft material comprises silicone, calcium, sodium or phosphate.

15. The method of claim 9, wherein the defect is a bone defect, and the graft material comprises bone graft material.

16. The method of claim 9, wherein the attribute is a recommended dosage by weight, and further including the step of calculating a target weight by determining the porosity of the graft material and a density value of the graft material.

17. The method of claim 16, wherein the step of calculating a target weight comprises determining a percentage value of volume occupied by the graft material.

18. The method of claim 9, wherein the graft material is in the form of fibers, particles, granules, clusters, or combinations thereof.

19. The method of claim 9, wherein the graft material comprises silicone, calcium, sodium, or phosphate.

20. The method of claim 9, wherein the defect is a bone defect, and the graft material comprises bone graft material.

21. A method of providing consistent, dose controlled application of a graft material to a defect, comprising:
providing a series of pre-sized containers of graft material, the containers having a range of volumes corresponding to a range of defect volumes, wherein recommended dosages by weight of the graft material corresponding to the range of defect volumes are provided in the respective container volumes;
performing a clinical evaluation to determine a volume of the defect;
selecting a pre-sized container of graft material based on the determined volume of the defect; and
applying the graft material of the selected container to the defect.

22. The method of claim 21, further comprising the step of forming a graft implant from the graft material of the selected container prior to the applying step.

23. The method of claim 21, wherein the graft material is in the form of fibers, particles, granules, clusters, or combinations thereof.

24. The method of claim 21, wherein the graft material comprises silicone, calcium, sodium or phosphate.

25. The method of claim 21, wherein the defect is a bone defect, and the graft material comprises bone graft material.

* * * * *